US00PP22184P2

(12) United States Plant Patent

Bak et al.

(10) Patent No.: US PP22,184 P2

(45) Date of Patent: Oct. 4, 2011

(54) *VRIESEA* PLANT NAMED 'SENSE'

(50) Latin Name: ***Vriesea* sp.**
Varietal Denomination: SENSE

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 0 days.

(21) Appl. No.: 12/802,272

(22) Filed: Jun. 3, 2010

(51) Int. Cl.
*A01H 5/00* (2006.01)

(52) U.S. Cl. ..... Plt./370

(58) Field of Classification Search ..... Plt./370
See application file for complete search history.

(56) References Cited

OTHER PUBLICATIONS

Printout of application information from Community Plant Variety Office (CPVO) website for corresponding CPVO application No. 2010/0785 filed Apr. 6, 2010 (1 page) (http://www.cpvoextranet.cpvo.europa.eu).
Printout of application information from Japanese Plant Breeders' Rights application database for corresponding application No. 24875 filed May 18, 2010 (1 page).

*Primary Examiner* — June Hwu
(74) *Attorney, Agent, or Firm* — Foley & Lardner LLP

(57) ABSTRACT

A new and distinct *Vriesea* sp. plant named 'SENSE', characterized as a funnel-form rosette plant, measuring about 32 cm in total height (when flowering) and about 30 cm to 35 cm in diameter; compound, Pink, closest to red-purple, RHS 60A, bipinate spike inflorescence, measuring about 13 cm to 24 cm in height and about 10-17 cm in diameter; about 1 to 5 branches, measuring about 5 cm to 10 cm in length and about 3.5 cm to 4.5 cm in width; and medium green foliage (RHS 137A), measuring about 24 cm in length and about 4.0 cm in width.

2 Drawing Sheets

Latin name of the genus and species of the plant claimed: *Vriesea* sp.

Variety denomination: 'SENSE'.

BACKGROUND OF THE INVENTION

The present invention relates to a new and distinct cultivar of *Vriesea* plant, botanically known as *Vriesea* sp., hereinafter referred to by the cultivar name 'SENSE'. The genus of *Vriesea* belongs to the Bromeliaceae family.

The new *Vriesea* 'SENSE' is a product of a planned breeding program conducted by the inventors, Elly Bak and Nico D. M. Steur, in Assendelft, The Netherlands. The objective of the breeding program is to develop a new *Vriesea* variety with good growing habit and attractive pink inflorescence.

The new *Vriesea* 'SENSE' originated from a cross-made in a controlled breeding program by the inventors in 1998 in Assendelft, The Netherlands. The female or seed parent is the *Vriesea* selection designated '89326' (unpatented), and the male or pollen parent is the *Vriesea* selection designated '93430' (unpatented). 'SENSE' was discovered and selected by the inventors in May of 2002, as a single flowering plant within the progeny of the stated cross in a controlled environment in Assendelft, The Netherlands.

Asexual reproduction of the new *Vriesea* 'SENSE' performed by vegetative means by tissue culture was first performed in 2004, in Assendelft, The Netherlands. The first 'SENSE' plants propagated through the use of tissue culture flowered in 2008, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'SENSE' which in combination distinguish this *Vriesea* as a new and distinct cultivar:

1. Funnel-form rosette plant, measuring about 32 cm in total height (when flowering) and about 30 cm to 35 cm in diameter;
2. Compound, pink (closest to red-purple, RHS 60A) bipinate spike inflorescence, measuring about 13 cm to 24 cm in height and about 10 to 17 cm in diameter;
3. About 1 to 5 branches, measuring about 5 cm to 10 cm in length and about 3.5 cm to 4.5 cm in width; and
4. Medium green foliage (RHS 137A), measuring about 24 cm in length and about 4.0 cm in width.

Plants of the parents, *Vriesea* sp. designated '89326' (unpatented) and *Vriesea* sp. designated '93420' (unpatented), are no longer available to provide a botanical comparison with the new *Vriesea* 'SENSE'.

Of the many commercial cultivars known to the present inventors, the most similar in comparison to the new *Vriesea* 'SENSE' is *Vriesea* sp. 'ENERGY' (patented, U.S. Plant Pat. No. 18,235). Plants of the new *Vriesea* 'SENSE' differ from plants of *Vriesea* 'ENERGY' primarily in inflorescence color. Plants of 'SENSE' produce pink inflorescence whereas plants of 'ENERGY' produce yellow inflorescence.

BRIEF DESCRIPTION OF THE PHOTOGRAPHS

The accompanying photographs illustrate the overall appearance of the new *Vriesea* 'SENSE' showing the colors as true as is reasonably possible with colored reproductions of this type. Colors in the photographs may differ slightly from the color values cited in the detailed botanical description which accurately describes the color of 'SENSE'.

DETAILED BOTANICAL DESCRIPTION

Figure 1:
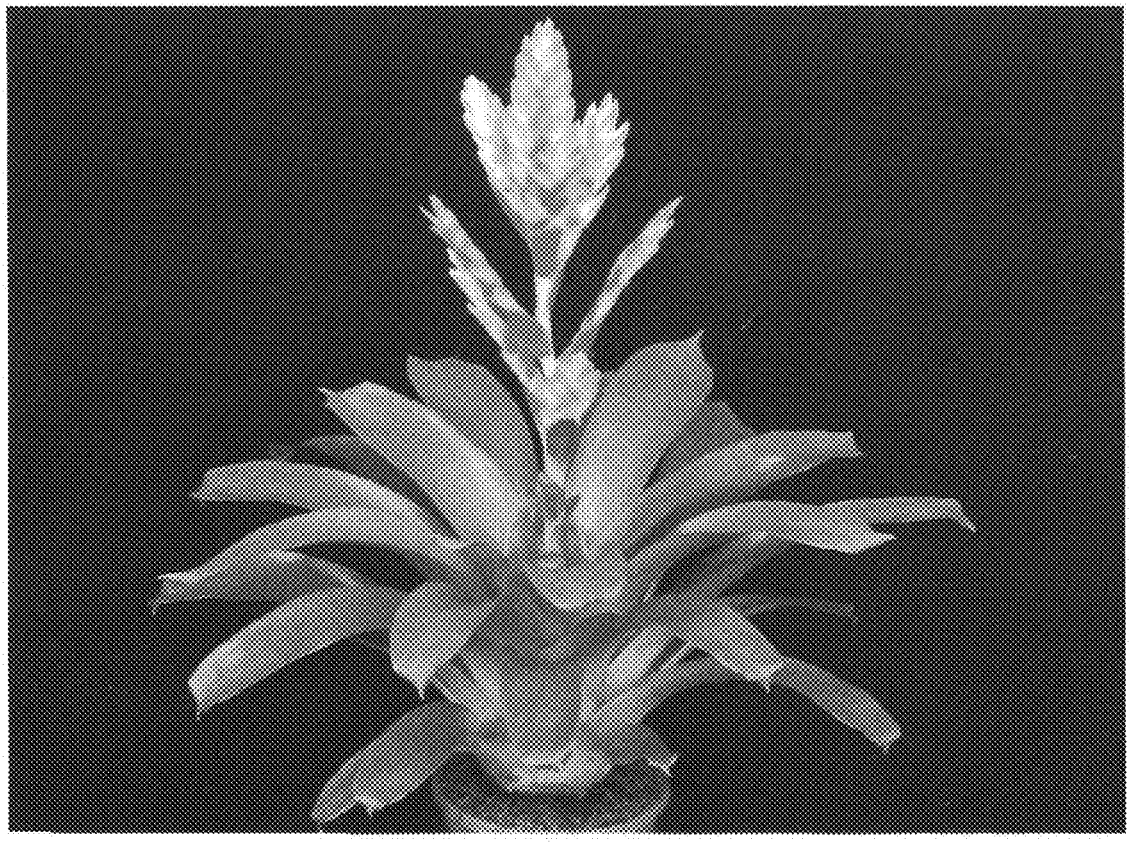
FIG. 1 shows a side view perspective of a typical potted flowering plant of 'SENSE' at about 17 months of age.
Figure 2:
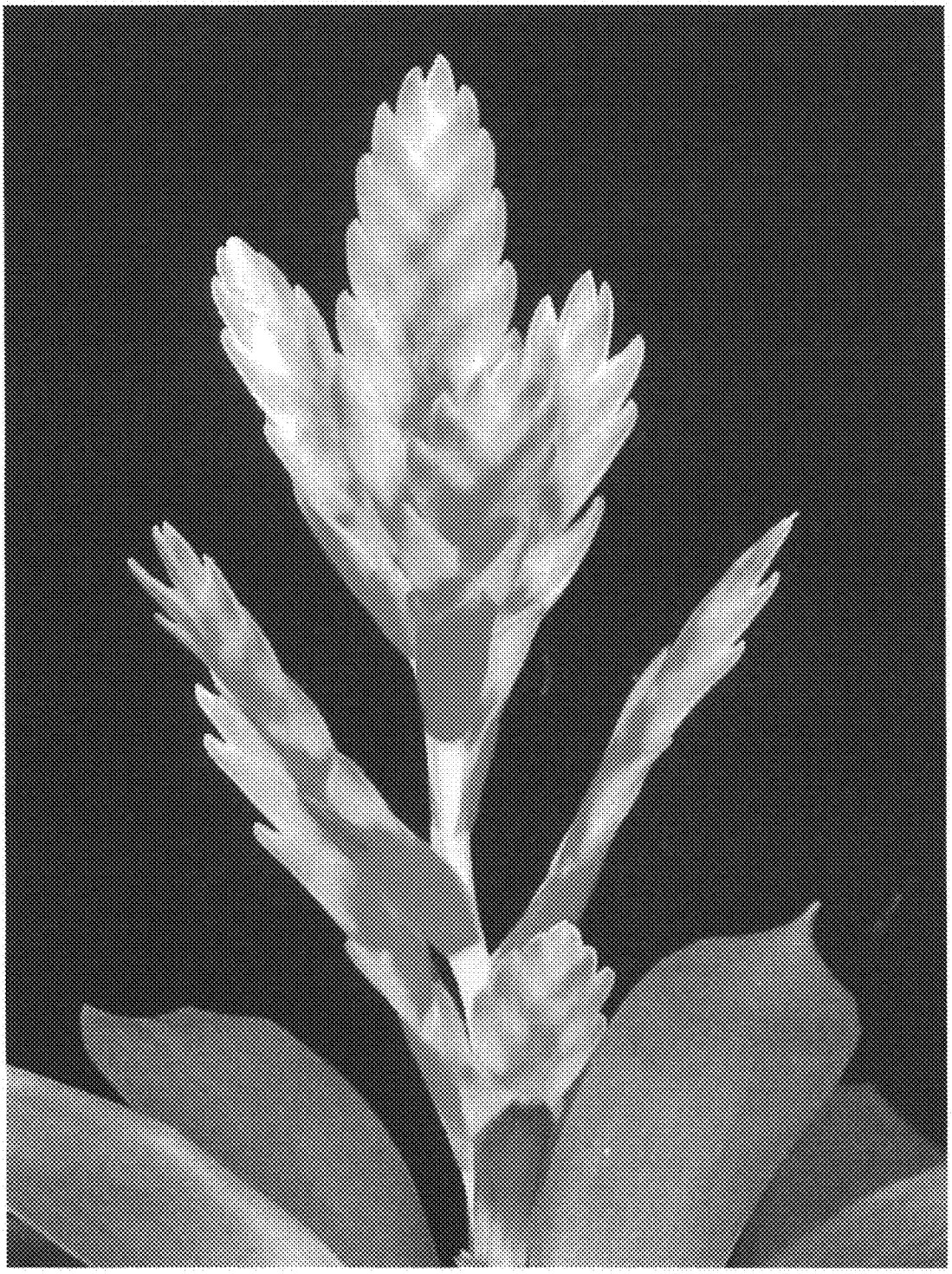
FIG. 2 shows a close-up side view perspective of the inflorescence of a typical potted flowering plant of 'SENSE' at about 17 months of age.

'SENSE' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Vriesea* 'SENSE' as grown in a greenhouse in Assendelft, The Netherlands, under conditions which closely approximate those generally used in commercial practice. Plants of 'SENSE' were grown in a greenhouse with day temperatures ranging from 20° C. to 28° C. and night temperatures ranging from 18° C. to 23° C. No artificial lighting or photoperiodic treatments were conducted, but plants of 'SENSE' are forced into flowering. The following fertilizer is added when growing plants of 'SENSE': 1 part nitrogen, 0.6 parts phosphor, 2 parts Kalium and 0.1 parts magnesium.

Color references are made to The Royal Horticultural Society Colour Chart (R.H.S.), 2001 Edition, except where general colors of ordinary significance are used. Color values were taken under daylight conditions in a greenhouse in Assendelft, The Netherlands. The age of the plants of 'SENSE' described is about 17 months.

Classification:

*Botanical.*—*Vriesea* sp.

Parentage:

*Female parent.*—*Vriesea* sp. designated '89326' (unpatented).

*Male parent.*—*Vriesea* sp. designated '93430' (unpatented).

Propagation: Tissue culture.

Plant:

*General appearance and form.*—Height: About 32 cm (when flowering). Width: About 30 cm to 35 cm. Shape: Funnel form rosette.

*Growth habit.*—Stemless.

*Plant vigor.*—Good.

*Flowering season.*—A fully grown plant can flower year round, starting 15-17 weeks after induction of natural light or trough flowering treatment.

*Cold tolerance.*—Frost tender. Temperatures below 5° C. may damage plants.

*Fragrance.*—None.

Foliage:

*Quantity.*—About 15 to 20.

*Size of mature leaf.*—Length: About 24 cm. Width: About 4.0 cm.

*Overall shape.*—Broad-linear.

*Apex shape.*—Abruptly acuminate.

*Base shape.*—Strap-like around central axis.

*Margin.*—Entire.

*Texture* (*both surfaces*).—Smooth and glabrous.

*Color.*—Leaf color can vary somewhat depending on growing conditions. Upper Surface: Mature leaf: Green, RHS 137A. Immature leaf: Yellow-green, RHS 146B. Lower Surface: Mature leaf: Yellow-green, RHS 146B. Immature leaf: Yellow-green, RHS 146B.

*Venation.*—None.

Inflorescence:

*Quantity and form.*—1 flower per floral bract, typical for the genus *Vriesea;* flowering is normally in progression from base to tip of scape.

*Shape.*—Erect, bipinate spike (main spike about 13 cm in length and about 6 cm in width; side spike about 8-12 cm in length and about 4-5 cm in width).

*Size.*—Height: About 13 cm to 24 cm. Diameter: About 10-17 cm.

*Corolla.*—Form: Long and narrow, petals and sepals fused at the base around the ovary. Number: About 20 to 40 depending on the size of plant.

*Petals.*—Number: 3 per flower. Length: About 4.0 cm. Width: About 0.8 cm. Overall Shape: Ligulate. Apex Shape: Obtuse. Base Shape: Fused. Color: Upper surface: Yellow, closest to RHS 6B. Lower surface: Yellow, closest to RHS 6B.

*Sepals.*—Number: 3 per flower. Length: About 2.5 cm. Width: About 0.9 cm. Overall Shape: Ligulate. Apex Shape: Acute. Base Shape: Fused. Color: Upper surface: Yellow, closest to RHS 6D. Lower surface: Yellow, closest to RHS 6D.

*Branches.*—Quantity: About 1 to 5 (depending on the size of the plant). Length: About 5 cm to 10 cm. Width: About 3.5 cm to 4.5 cm. Color: Pink, closest to red-purple, RHS 60A.

*Bracts.*—Quantity of bracts on main spike: About 12. Arrangement: Alternate. Size: Length: About 4.0 cm. Width: About 3.0 cm. Overall shape: Ovate, folded double in length (around the petals).

*Primary bract color.*—Pink, closest to red-purple, RHS 60A.

Reproductive organs:

*Androecium.*—Stamen: Number: 6 per flower. Length: About 4.5 cm. Diameter: About 0.1 cm. Color: Yellow, closest to RHS 4C. Anther: Length: About 0.6 cm. Color: Yellow, closest to RHS 6B. Pollen: Amount: Too small to count. Color: Yellow, too small to qualify RHS value.

*Gynoecium.*—Pistil: Number: 1 per flower. Length: About 5.3 cm.

*Stigma.*—Shape: 3-parted. Width: About 0.3 cm. Color: Yellow, closest to RHS 4B.

*Style.*—Length: About 4.5 cm. Color: Yellow, closest to RHS 4B.

*Ovary.*—Shape: Conical. Length: About 0.6 cm. Diameter: About 0.3 cm. Color: Yellow, closest to RHS 4B.

Seeds: None produced.

Fruit: None produced.

Disease/pest resistance: No information is currently available.

Disease/pest susceptibility: No information is currently available.

What is claimed is:

1. A new and distinct *Vriesea* sp. plant named 'SENSE', as illustrated and described herein.

* * * * *